(12) United States Patent
Johnston et al.

(10) Patent No.: US 8,877,987 B2
(45) Date of Patent: Nov. 4, 2014

(54) PROCESS FOR PRODUCING ANHYDROUS ETHANOL USING EXTRACTIVE DISTILLATION COLUMN

(75) Inventors: Victor J. Johnston, Houston, TX (US); David Lee, Seabrook, TX (US); Lincoln Sarager, Houston, TX (US); R. Jay Warner, Houston, TX (US)

(73) Assignee: Celanese International Corportation, Dallas, TX (US)

( * ) Notice: Subject to any disclaimer, the term of this patent is extended or adjusted under 35 U.S.C. 154(b) by 574 days.

(21) Appl. No.: 13/197,759

(22) Filed: Aug. 3, 2011

(65) Prior Publication Data

US 2013/0035525 A1 Feb. 7, 2013

(51) Int. Cl.
| | |
|---|---|
| *C07C 31/08* | (2006.01) |
| *B01D 3/40* | (2006.01) |
| *B01D 3/14* | (2006.01) |
| *C07C 29/149* | (2006.01) |
| *C07C 29/80* | (2006.01) |
| *C07C 29/84* | (2006.01) |

(52) U.S. Cl.
CPC *B01D 3/40* (2013.01); *B01D 3/148* (2013.01); *C07C 29/149* (2013.01); *C07C 29/80* (2013.01); *C07C 29/84* (2013.01)
USPC ............ 568/890; 568/881; 568/884; 568/885

(58) Field of Classification Search
None
See application file for complete search history.

(56) References Cited

U.S. PATENT DOCUMENTS

| | | | |
|---|---|---|---|
| 1,469,447 A | 10/1923 | Schneible | |
| 2,591,671 A | 4/1952 | Catterall | |
| 2,591,672 A | 4/1952 | Catterall | |
| 2,649,407 A | 8/1953 | Harrison et al. | |
| 2,702,783 A | 2/1955 | Harrison et al. | |
| 2,744,939 A | 5/1956 | Kennel | |
| 2,882,244 A | 4/1959 | Milton | |
| 2,901,404 A | 8/1959 | Kirshenbaum et al. | |
| 3,130,007 A | 4/1964 | Breck | |
| 3,408,267 A | 10/1968 | Miller et al. | |
| 3,445,345 A | 5/1969 | Katzen et al. | |
| 3,478,112 A | 11/1969 | Karl et al. | |
| 3,990,952 A | 11/1976 | Katzen et al. | |
| 4,149,940 A | 4/1979 | Pinto | |
| 4,275,228 A | 6/1981 | Gruffaz et al. | |
| 4,306,942 A | 12/1981 | Brush et al. | |
| 4,317,918 A | 3/1982 | Takano et al. | |
| 4,319,058 A | 3/1982 | Kulprathipanja et al. | |
| 4,379,028 A | 4/1983 | Berg et al. | |
| 4,395,576 A | 7/1983 | Kwantes et al. | |
| 4,398,039 A | 8/1983 | Pesa et al. | |
| 4,421,939 A | 12/1983 | Kiff et al. | |
| 4,422,903 A | 12/1983 | Messick et al. | |
| 4,428,798 A | 1/1984 | Zudkevitch et al. | |
| 4,454,358 A | 6/1984 | Kummer et al. | |
| 4,455,198 A | 6/1984 | Zudkevitch et al. | |
| 4,465,854 A | 8/1984 | Pond et al. | |
| 4,465,875 A | 8/1984 | Greenbank et al. | |
| 4,471,136 A | 9/1984 | Larkins et al. | |
| 4,480,115 A | 10/1984 | McGinnis | |
| 4,492,808 A | 1/1985 | Hagen et al. | |
| 4,497,967 A | 2/1985 | Wan | |
| 4,517,391 A | 5/1985 | Schuster et al. | |
| 4,520,213 A | 5/1985 | Victor | |
| 4,541,897 A | 9/1985 | Sommer et al. | |
| 4,559,109 A | 12/1985 | Lee et al. | |
| 4,569,726 A | 2/1986 | Berg et al. | |
| 4,626,321 A | 12/1986 | Grethlein et al. | |
| 4,631,115 A | 12/1986 | Berg et al. | |
| 4,654,123 A | 3/1987 | Berg et al. | |
| 4,678,543 A | 7/1987 | Houben et al. | |
| 4,692,218 A | 9/1987 | Houben et al. | |
| 4,777,303 A | 10/1988 | Kitson et al. | |
| 4,804,791 A | 2/1989 | Kitson et al. | |
| 4,826,795 A | 5/1989 | Kitson et al. | |
| 4,842,693 A | 6/1989 | Wheldon | |
| 4,961,826 A | 10/1990 | Grethlein et al. | |
| 4,978,778 A | 12/1990 | Isshiki et al. | |
| 4,985,572 A | 1/1991 | Kitson et al. | |
| 4,990,655 A | 2/1991 | Kitson et al. | |
| 4,994,608 A | 2/1991 | Torrence et al. | |
| 5,001,259 A | 3/1991 | Smith et al. | |
| 5,026,908 A | 6/1991 | Smith et al. | |
| 5,035,776 A | 7/1991 | Knapp | |
| 5,061,671 A | 10/1991 | Kitson et al. | |

(Continued)

FOREIGN PATENT DOCUMENTS

| | | |
|---|---|---|
| EP | 0104197 | 4/1984 |
| EP | 0137749 | 4/1985 |

(Continued)

OTHER PUBLICATIONS

Response to Final Office Action for U.S. Appl. No. 13/162,005, filed Nov. 26, 2013.
Response to Final Office Action for U.S. Appl. No. 13/162,034, filed Nov. 27, 2013.
Kumar, et al., "Anhydrous ethanol: A renewable source of energy", Renewable and Sustainable Energy Reviews, Elseviers Science, vol. 14, No. 7, Sep. 1, 2010, pp. 1830-1844.
International Search Report and Written Opinion for PCT/US2011/046495 mailed Oct. 4, 2012.
Zheng, et al. (2007). Preparation and catalytic properties of a bimetallic Sn—Pt complex in the supercages of NaY zeolite by use of surface organometallic chemistry, Applied Organometallic Chemistry, 21(10), 836-840.

(Continued)

Primary Examiner — Sudhakar Katakam

(57) ABSTRACT

The present invention relates to the recovery of ethanol from a crude ethanol product obtained from the hydrogenation of acetic acid. Separation and purification processes of crude ethanol product are employed to allow recovery of an anhydrous ethanol composition. The process involves separating the crude ethanol product using one or more extractive distillation columns that employ one or more extractive agents. The anhydrous ethanol composition comprises less than 1 wt. % water, based on the total weight of the anhydrous ethanol composition.

18 Claims, 2 Drawing Sheets

(56) References Cited

U.S. PATENT DOCUMENTS

| | | |
|---|---|---|
| 5,124,004 A | 6/1992 | Grethlein et al. |
| 5,144,068 A | 9/1992 | Smith et al. |
| 5,149,680 A | 9/1992 | Kitson et al. |
| 5,185,481 A | 2/1993 | Muto et al. |
| 5,215,902 A | 6/1993 | Tedder |
| 5,227,141 A | 7/1993 | Kim et al. |
| 5,233,099 A | 8/1993 | Tabata et al. |
| 5,237,108 A | 8/1993 | Marraccini et al. |
| 5,250,271 A | 10/1993 | Horizoe et al. |
| 5,348,625 A | 9/1994 | Berg |
| 5,415,741 A | 5/1995 | Berg |
| 5,437,770 A | 8/1995 | Berg |
| 5,445,716 A | 8/1995 | Berg |
| 5,449,440 A | 9/1995 | Rescalli et al. |
| RE35,377 E | 11/1996 | Steinberg et al. |
| 5,599,976 A | 2/1997 | Scates et al. |
| 5,762,765 A | 6/1998 | Berg |
| 5,770,770 A | 6/1998 | Kim et al. |
| 5,800,681 A | 9/1998 | Berg |
| 5,821,111 A | 10/1998 | Grady et al. |
| 5,993,610 A | 11/1999 | Berg |
| 6,121,498 A | 9/2000 | Tustin et al. |
| 6,143,930 A | 11/2000 | Singh et al. |
| 6,232,352 B1 | 5/2001 | Vidalin et al. |
| 6,294,703 B1 | 9/2001 | Hara et al. |
| 6,375,807 B1 * | 4/2002 | Nieuwoudt et al. ............ 203/19 |
| 6,509,180 B1 | 1/2003 | Verser et al. |
| 6,627,770 B1 | 9/2003 | Cheung et al. |
| 6,657,078 B2 | 12/2003 | Scates et al. |
| 6,685,754 B2 | 2/2004 | Kindig et al. |
| 6,693,213 B1 | 2/2004 | Kolena et al. |
| 6,723,886 B2 | 4/2004 | Allison et al. |
| 6,809,217 B1 * | 10/2004 | Colley et al. .................. 560/231 |
| 6,906,228 B2 | 6/2005 | Fischer et al. |
| 6,927,048 B2 | 8/2005 | Verser et al. |
| 7,005,541 B2 | 2/2006 | Cheung et al. |
| 7,074,603 B2 | 7/2006 | Verser et al. |
| 7,115,772 B2 | 10/2006 | Picard et al. |
| 7,208,624 B2 | 4/2007 | Scates et al. |
| 7,297,236 B1 | 11/2007 | Vander Griend et al. |
| 7,351,559 B2 | 4/2008 | Verser et al. |
| 7,399,892 B2 | 7/2008 | Rix et al. |
| 7,507,562 B2 | 3/2009 | Verser et al. |
| 7,553,397 B1 | 6/2009 | Colley et al. |
| 7,572,353 B1 | 8/2009 | Vander Griend |
| 7,601,865 B2 | 10/2009 | Verser et al. |
| 7,608,744 B1 | 10/2009 | Johnston et al. |
| 7,682,812 B2 | 3/2010 | Verser et al. |
| 7,732,173 B2 | 6/2010 | Mairal et al. |
| 7,744,727 B2 | 6/2010 | Blum et al. |
| 7,863,489 B2 | 1/2011 | Johnston et al. |
| 7,884,253 B2 | 2/2011 | Stites et al. |
| 7,888,082 B2 | 2/2011 | Verser et al. |
| 2006/0019360 A1 | 1/2006 | Verser et al. |
| 2006/0127999 A1 | 6/2006 | Verser et al. |
| 2007/0031954 A1 | 2/2007 | Mairal et al. |
| 2007/0270511 A1 | 11/2007 | Melnichuk et al. |
| 2008/0135396 A1 | 6/2008 | Blum |
| 2008/0193989 A1 | 8/2008 | Verser et al. |
| 2009/0014313 A1 | 1/2009 | Lee et al. |
| 2009/0023192 A1 | 1/2009 | Verser et al. |
| 2009/0069609 A1 | 3/2009 | Kharas et al. |
| 2009/0081749 A1 | 3/2009 | Verser et al. |
| 2009/0166172 A1 | 7/2009 | Casey et al. |
| 2009/0281354 A1 | 11/2009 | Mariansky et al. |
| 2009/0318573 A1 | 12/2009 | Stites et al. |
| 2010/0029980 A1 | 2/2010 | Johnston et al. |
| 2010/0029995 A1 | 2/2010 | Johnston et al. |
| 2010/0030001 A1 | 2/2010 | Chen et al. |
| 2010/0030002 A1 | 2/2010 | Johnston et al. |
| 2010/0121114 A1 | 5/2010 | Johnston et al. |
| 2010/0185021 A1 | 7/2010 | Ross et al. |
| 2010/0197485 A1 | 8/2010 | Johnston et al. |
| 2011/0082322 A1 | 4/2011 | Jevtic et al. |
| 2012/0273338 A1 | 11/2012 | Lee |
| 2012/0323049 A1 | 12/2012 | Lee |
| 2012/0323050 A1 | 12/2012 | Lee |

FOREIGN PATENT DOCUMENTS

| | | |
|---|---|---|
| EP | 0167300 | 1/1986 |
| EP | 0456647 | 11/1991 |
| EP | 0990638 | 4/2000 |
| EP | 2060553 | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| JP | 4-193304 | 7/1992 |
| WO | WO 83/03409 | 10/1983 |
| WO | WO 2007/003897 | 1/2007 |
| WO | WO 2008/135192 | 11/2008 |
| WO | WO 2009/009322 | 1/2009 |
| WO | WO 2009/009323 | 1/2009 |
| WO | WO 2009/048335 | 4/2009 |
| WO | WO 2009/063176 | 5/2009 |
| WO | WO 2009/105860 | 9/2009 |
| WO | WO 2010/014151 | 2/2010 |
| WO | WO 2010/055285 | 5/2010 |
| WO | WO 2011/053365 | 5/2011 |
| WO | WO 2011/097214 | 8/2011 |

OTHER PUBLICATIONS

ZeaChem, Inc., Technology Overview, Lakewood, Colorado www.zeachem.com, 2008.

Udeye et al., "Ethanol heterogeneousazeotrophic distillation design and construction," International Journal of Physical Sciences, vol. 4 (3), Mar. 2009, pp. 101-106.

Santori et al.(2000). Hydrogenation of carbonylic compounds on Pt/SiO2 catalysts modified with SnBu4, Studies in Surface Science and Catalysis, 130, 2063-2068.

Rachmady, Acetic Acid Reduction by H2 on Bimetallic Pt—Fe Catalysts, Journal of Catalysis 209, 87-98 (Apr. 1, 2002), Elsevier Science (USA).

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Hilmen, Separation of Azeotropic Mixtures: Tools for Analysis and Studies on Batch Distillation Operation (Nov. 2000) p. 17-20.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Amit M. Goda et al., DFT modeling of selective reduction of acetic acid to acetaldehyde on Pt-based bimetallic catalysts, 20th NAM, Houston, TX, Jun. 17-22, 2007 available online at <http://www.nacatsoc.org/20nam/abstracts/O-S9-18.pdf>.

Alcala, et al., (2005). Experimental and DFT studies of the conversion of ethanol and acetic acid on PtSn-based catalysts, Journal of Physical Chemistry, 109(6), 2074-2085.

International Search Report and Written Opinion for PCT/US2011/023328 mailed Aug. 5, 2011.

International Preliminary Report on Patentability for PCT/US2011/046495 mailed Feb. 13, 2014.

* cited by examiner

PROCESS FOR PRODUCING ANHYDROUS ETHANOL USING EXTRACTIVE DISTILLATION COLUMN

FIELD OF THE INVENTION

The present invention relates generally to processes for producing an anhydrous ethanol composition. In particular, the present invention relates to processes for producing an anhydrous ethanol composition via hydrogenation of acetic acid and the use of extractive distillation column.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Anhydrous ethanol is preferred for some applications, e.g., fuels. Anhydrous or substantially anhydrous ethanol, however, is often difficult to obtain from conventional hydrogenation and separation processes. Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are formed with ethanol or are formed in side reactions. These impurities limit the production and recovery of ethanol from such reaction mixtures. For example, the ethanol and water produced in conventional hydrogenation reactions may form a binary azeotrope. This azeotrope contains about 95% ethanol and about 5% water. Because the boiling point of this azeotrope (78° C.) is just slightly below that of pure ethanol (78.4° C.), an anhydrous or substantially anhydrous ethanol composition is difficult to obtain from a crude ethanol composition via simple, conventional distillation.

Therefore, a need remains for an improved process and system for the recovery of anhydrous ethanol composition from a crude product obtained by reducing alkanoic acids, such as acetic acid, and/or other carbonyl group-containing compounds.

SUMMARY OF THE INVENTION

In a first embodiment, the present invention is directed to a process for purifying a crude ethanol product. The process comprises the step of hydrogenating an acetic acid feed stream in a reactor in the presence of a catalyst to form a crude ethanol product. The process further comprises the steps of separating at least a portion of the crude ethanol product in a first column to yield a first distillate and a first residue. In one embodiment, the first distillate comprises ethanol, water and ethyl acetate and the first residue comprises acetic acid. The process also comprises the step of separating at least a portion of the first distillate in a second column to yield a second distillate and a second residue. The second distillate comprises ethyl acetate and the second residue comprises ethanol and water. The process further comprises the step of dehydrating at least a portion of the second residue via extractive to yield an anhydrous ethanol stream comprising less than 1 wt. % water.

Preferably, the dehydrating step comprises separating in a third column, e.g., an extractive distillation column, at least a portion of the second residue into a third distillate and a third residue. When the third column is an extractive distillation column, this column may utilize an extractive agent.

In a second embodiment, the present invention is directed to a system for producing an anhydrous ethanol composition. The system comprises a reactor for hydrogenating acetic acid in the presence of a catalyst to form a crude ethanol product. The system further comprises a first column for separating at least a portion of the crude ethanol product into a first distillate comprising ethanol, water and ethyl acetate, and a first residue comprising acetic acid. In one embodiment, the system comprises a second column for separating at least a portion of the crude ethanol product into a second distillate comprising ethyl acetate and a second residue comprising ethanol and water. The system further comprises a dehydrator for dehydrating at least a portion of the second residue to form the anhydrous ethanol composition less that 1 wt. % water.

In a third embodiment, the present invention is directed to a process for producing anhydrous ethanol. The process comprises the step of hydrogenating acetic acid in the reactor in the presence of a catalyst to form a crude ethanol product. The process further comprises separating at least a portion of the crude ethanol product to yield a first distillate comprising ethanol, ethyl acetate and water. In an embodiment, the process comprises separating at least a portion of the first distillate in a second distillation column to yield a second distillate comprising ethyl acetate and a second residue comprising ethanol and water. The process further comprises dehydrating at least a portion of the second residue in a third distillation column to yield an anhydrous ethanol composition comprising less that 1 wt. % water and an extractive agent stream comprising an extractive agent and recovering at least a portion of the extractive agent from the extractive agent stream.

BRIEF DESCRIPTION OF DRAWINGS

The invention is described in detail below with reference to the appended drawings, wherein like numerals designate similar parts.

DETAILED DESCRIPTION OF THE INVENTION

Figure 1:
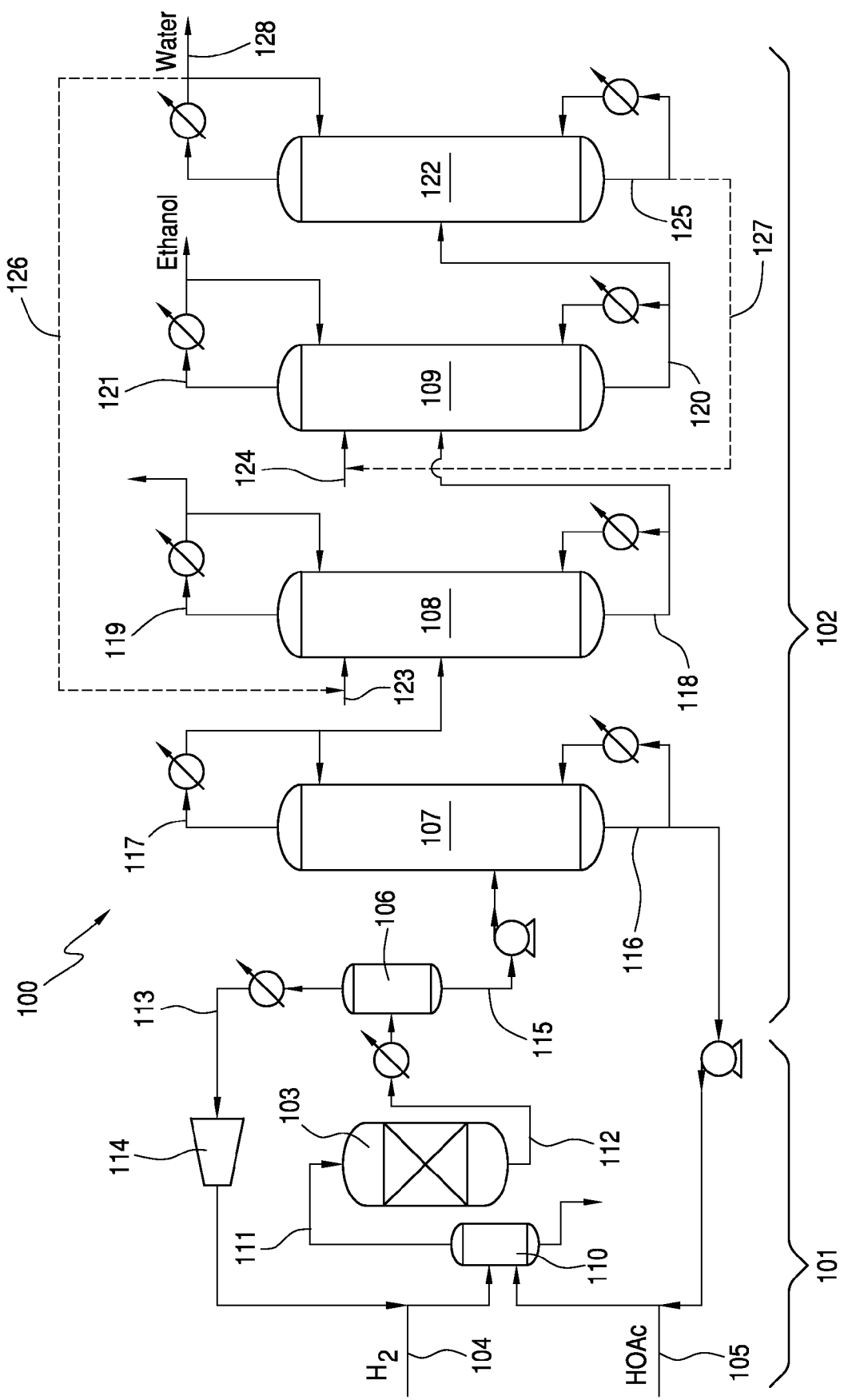
FIG. 1 is a schematic diagram of a hydrogenation system in accordance with one embodiment of the present invention.

The present invention relates to processes for recovering an anhydrous ethanol composition from a crude ethanol product. In particular, the present invention relates to processes for recovering an anhydrous ethanol composition from a crude ethanol product, which preferably is formed by hydrogenating acetic acid in the presence of a catalyst. The anhydrous ethanol composition may be separated using one or more separation units, e.g., distillation columns, e.g., two or more, or three or more.

In a preferred embodiment, the process includes the step of dehydrating an ethanol enriched stream derived from the crude ethanol product to yield the anhydrous ethanol composition using one or more extractive distillation columns. Typically, ethanol compositions as formed contain a certain amount of water and, as such, are not suitable for fuel purposes. To alleviate this problem, the inventive process employs an extractive distillation column to produce the anhydrous ethanol composition. In one embodiment, the extractive distillation column(s) utilize an extractive agent. In addition, since binary and ternary azeotropes may form between two or more of ethyl acetate, ethanol and water in the crude ethanol product or a processed stream thereof, the process may employ an additional extractive distillation column to facilitate separation of these components. In these embodiments, ethanol may be separated from the crude ethanol product even when the content of ethyl acetate and/or water in the crude ethanol product is sufficient to form such azeotropes.

Preferably, the dehydrating step comprises separating in a third column, e.g., an extractive distillation column, at least a portion of the second residue into a third distillate and a third residue. When the third column is an extractive distillation column, this column may utilize an extractive agent. In one embodiment, the extractive agent employed may be provided from an external source. In another embodiment, the extractive agent may be provided from at least a portion of an in-process recycle stream. For example, the extractive agent may comprise a recycled stream from an extractive agent recovery column that separates the extractive agent from anhydrous ethanol or water. Of course, combinations of these sources are possible as well.

The selection of the extractive agent may affect the separation operation of the extractive column. As such, in one embodiment, the third distillate may comprise the anhydrous ethanol composition and the third residue comprises water, while in another embodiment, the third distillate may comprise water and the third residue comprises the anhydrous ethanol composition. For example, when a high-boiling water selective extractive agent is employed, the third distillate may comprise the anhydrous ethanol composition and the third residue may comprise water. As another example, when a high-boiling ethanol selective extractive agent is employed, the third distillate may comprise water and the third residue may comprise the anhydrous ethanol composition. Beneficially, the present invention provides increased ability to control the separation operations of the third column, e.g., extractive distillation column, which provides better opportunities to integrate the third column streams with other separation zone components.

The extractive agent employed in the extractive distillation column may be recovered downstream in an extractive agent recovery column. Depending on the conditions in the recovery column, the recovered extractive agent may comprise at least a portion of the residue or at least a portion of the distillate from the recovery column. Without being bound to theory, it is believed that the stream comprising the recovered extractive agent may better promote separation in the extractive distillation column(s). As such, in one embodiment, the recovered extractive agent may better facilitate the separation of ethanol from the crude ethanol product, and, accordingly may better facilitate production of the anhydrous ethanol composition. As an added benefit, the process of the present invention may improve overall process efficiency and reduce cost by decreasing water use and/or consumption. Further, the ability to recycle water may promote heat integration throughout the system, which reduces energy consumption.

Embodiments of the present invention beneficially may be used in applications for recovery and/or purifying of ethanol on an industrial scale.

In a preferred embodiment, the anhydrous ethanol composition comprises ethanol and less than 1 wt. % water, e.g., less than 0.5 wt. %, less than 0.1 wt. %, less than 0.01 wt. %, less than 0.001 wt. % or less than 0.0001 wt. %, based on the total weight of the anhydrous ethanol composition. In terms of ranges, depending on the dehydration technique employed, the anhydrous ethanol composition may comprise from 0.0001 wt. % to 1 wt. % water, e.g., from 0.001 wt. % to 0.5 wt. % or from 0.001 wt. % to 0.05 wt. %, based on the total weight of the anhydrous ethanol composition. Preferably, the anhydrous ethanol composition formed by the inventive process comprises from 95 wt. % to 99.9999 wt. % ethanol and from 0.0001 wt. % to 1 wt. % water.

Hydrogenation Process

The process of the present invention may be used with any hydrogenation process for producing ethanol. The materials, catalysts, reaction conditions, and separation processes that may be used in the hydrogenation of acetic acid are described further below.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming syngas, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolyzed with additional natural gas to form syngas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into syngas, and U.S. Pat. No. 6,685,754, which discloses a method for the production of a hydrogen-containing gas composition, such as a syngas including hydrogen and carbon monoxide, are incorporated herein by reference in their entireties.

The acetic acid fed to the hydrogenation reaction may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Some embodiments of the process of hydrogenating acetic acid to form ethanol a variety of configuration using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 1500 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 hr$^{-1}$ or 6,500 hr$^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The hydrogenation of acetic acid to form ethanol is preferably conducted in the presence of a hydrogenation catalyst. Suitable hydrogenation catalysts include catalysts comprising a first metal and optionally one or more of a second metal, a third metal or any number of additional metals, optionally on a catalyst support. The first and optional second and third metals may be selected from Group IB, IIB, IIIB, IVB, VB, VIIB, VIIB, VIII transition metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin silver/palladium, copper/palladium, copper/zinc, nickel/palladium, gold/palladium, ruthenium/rhenium, and ruthenium/iron. Exemplary catalysts are further described in U.S. Pat. No. 7,608,744 and U.S. Pub. No. 2010/0029995, the entireties of which are incorporated herein by reference. In another embodiment, the catalyst comprises a Co/Mo/S catalyst of the type described in U.S. Pub. No. 2009/0069609, the entirety of which is incorporated herein by reference.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal preferably is from 0.05 to 4 wt. %, e.g., from 0.1 to 3 wt. %, or from 0.1 to 2 wt. %.

In addition to one or more metals, in some embodiments of the present invention the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 97 wt. %, or from 80 to 95 wt. %. In preferred embodiments that utilize a modified support, the support modifier is present in an amount from 0.1 to 50 wt. %, e.g., from 0.2 to 25 wt. %, from 0.5 to 15 wt. %, or from 1 to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $Co_2O_3$, $Bi_2O_3$.

In another embodiment, the support modifier may be a basic modifier that has a low volatility or no volatility. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

A preferred silica support material is SS61138 High Surface Area (HSA) Silica Catalyst Carrier from Saint Gobain Nor Pro. The Saint-Gobain Nor Pro SS61138 silica exhibits the following properties: contains approximately 95 wt. % high surface area silica; surface area of about 250 $m^2/g$; median pore diameter of about 12 nm; average pore volume of about 1.0 $cm^3/g$ as measured by mercury intrusion porosimetry and a packing density of about 0.352 $g/cm^3$ (22 $lb/ft^3$).

A preferred silica/alumina support material is KA-160 silica spheres from Sud Chemie having a nominal diameter of about 5 mm, a density of about 0.562 g/ml, an absorptivity of about 0.583 g $H_2O$/g support, a surface area of about 160 to 175 $m^2/g$, and a pore volume of about 0.68 ml/g.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485 referred to above, the entireties of which are incorporated herein by reference.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a mole percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. Preferred embodiments of the hydrogenation process have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram catalyst per hour or from 600 to 2,000 grams of ethanol per kilogram catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 1 ton of ethanol per hour, e.g., at least 15 tons of ethanol per hour or at least 30 tons of ethanol per hour. In terms of ranges, for large scale industrial production of ethanol, the process of the present invention may produce from 0.1 to 160 tons of ethanol per hour, e.g., from 15 to 160 tons of ethanol per hour or from 30 to 80 tons of ethanol per hour. Ethanol production from fermentation, due the economies of scale, typically does not permit the single facility ethanol production that may be achievable by employing embodiments of the present invention.

In various embodiments of the present invention, the crude ethanol product produced by the hydrogenation process, before any subsequent processing, such as purification and separation, will typically comprise unreacted acetic acid, ethanol and water. As used herein, the term "crude ethanol product" refers to any composition comprising from 5 to 70 wt. % ethanol and from 5 to 40 wt. % water. In some exemplary embodiments, the crude ethanol product comprises ethanol in an amount from 5 to 70 wt. %, e.g., from 10 to 60 wt. %, or from 15 to 50 wt. %, based on the total weight of the crude ethanol product. Preferably, the crude ethanol product contains at least 10 wt. % ethanol, at least 15 wt. % ethanol or at least 20 wt. % ethanol. The crude ethanol product typically will further comprise unreacted acetic acid, depending on conversion, for example, in an amount of less than 90 wt. %, e.g., less than 80 wt. % or less than 70 wt. %. In terms of ranges, the unreacted acetic acid optionally is present in the crude ethanol product in an amount from 0 to 90 wt. %, e.g., from 5 to 80 wt. %, from 15 to 70 wt. %, from 20 to 70 wt. % or from 25 to 65 wt. %. As water is formed in the reaction process, water will generally be present in the crude ethanol product, for example, in amounts ranging from 5 to 40 wt. %, e.g., from 10 to 30 wt. % or from 10 to 26 wt. %.

Ethyl acetate may also be produced during the hydrogenation of acetic acid or through side reactions and may be present, for example, in amounts ranging from 0 to 30 wt. %, e.g., from 0 to 20 wt. %, from 1 to 12 wt. % or from 3 to 10 wt. %. Acetaldehyde may also be produced through side reactions and may be present, for example, in amounts ranging from 0 to 10 wt. %, e.g., from 0 to 3 wt. %, from 0.1 to 3 wt. % or from 0.2 to 2 wt. %. Other components, such as, for example, esters, ethers, aldehydes, ketones, alkanes, and carbon dioxide, if detectable, collectively may be present in amounts less than 10 wt. %, e.g., less than 6 wt. % or less than 4 wt. %. In terms of ranges, other components may be present in an amount from 0.1 to 10 wt. %, e.g., from 0.1 to 6 wt. %, or from 0.1 to 4 wt. %. Exemplary component ranges for the crude ethanol product are provided in Table 1.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 15 to 70 | 15 to 50 | 25 to 50 |
| Acetic Acid | 0 to 90 | 0 to 50 | 15 to 70 | 20 to 70 |
| Water | 5 to 40 | 5 to 30 | 10 to 30 | 10 to 26 |
| Ethyl Acetate | 0 to 30 | 0 to 20 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product comprises acetic acid in an amount less than 20 wt. %, e.g., less than 15 wt. %, less than 10 wt. % or less than 5 wt. %. In embodiments having lower amounts of acetic acid, the conversion of acetic acid is preferably greater than 50%, e.g., greater than 75% or greater than 90%. In addition, the selectivity to ethanol may also be preferably high, and is preferably greater than 50%, e.g., greater than 75% or greater than 90%.

Ethanol Recovery

FIG. 1 shows a hydrogenation system 100 suitable for the hydrogenation of acetic acid and separating ethanol from the crude reaction mixture according to one embodiment of the invention. System 100 comprises reaction zone 101 and distillation zone 102. Reaction zone 101 comprises reactor 103, hydrogen feed line 104 and acetic acid feed line 105. Distillation zone 102 comprises flasher 106, first column 107, second column 108, a dehydrator, which is shown as third column 109, and fourth column 122.

Hydrogen and acetic acid are fed to a vaporizer 110 via lines 104 and 105, respectively, to create a vapor feed stream in line 111 that is directed to reactor 103. In one embodiment, lines 104 and 105 may be combined and jointly fed to the vaporizer 110, e.g., in one stream containing both hydrogen and acetic acid. The temperature of the vapor feed stream in line 111 is preferably from 100° C. to 350° C., e.g., from 120° C. to 310° C. or from 150° C. to 300° C. Any feed that is not vaporized is removed from vaporizer 110, as shown in FIG. 1, and may be recycled thereto. In addition, although FIG. 1 shows line 111 being directed to the top of reactor 103, line 111 may be directed to the side, upper portion, or bottom of reactor 103. Further modifications and additional components to reaction zone 101 are described below.

Reactor 103 contains the catalyst that is used in the hydrogenation of the carboxylic acid, preferably acetic acid. In one embodiment, one or more guard beds (not shown) may be used to protect the catalyst from poisons or undesirable impurities contained in the feed or return/recycle streams. Such guard beds may be employed in the vapor or liquid streams. Suitable guard bed materials are known in the art and include, for example, carbon, silica, alumina, ceramic, or resins. In one aspect, the guard bed media is functionalized to trap particular species such as sulfur or halogens. During the hydrogenation process, a crude ethanol product stream is withdrawn, preferably continuously, from reactor 103 via line 112. The crude ethanol product stream may be condensed and fed to flasher 106, which, in turn, provides a vapor stream and a liquid stream. The flasher 106 in one embodiment preferably operates at a temperature of from 50° C. to 500° C., e.g., from 70° C. to 400° C. or from 100° C. to 350° C. In one embodiment, the pressure of flasher 106 preferably is from 50 kPa to 2000 kPa, e.g., from 75 kPa to 1500 kPa or from 100 kPa to 1000 kPa. In one preferred embodiment the temperature and pressure of the flasher is similar to the temperature and pressure of the reactor 103.

The vapor stream exiting the flasher may comprise hydrogen and hydrocarbons, which may be purged and/or returned to reaction zone 101 via line 113. As shown in FIG. 1, the returned portion of the vapor stream passes through compressor 114 and is combined with the hydrogen feed and co-fed to vaporizer 110.

The liquid from flasher 106 is withdrawn and pumped via line 115 to the side of first column 107, also referred to as the acid separation column. In one embodiment, the contents of line 115 may be substantially similar to the crude ethanol product obtained from the reactor, except that the composition has substantially no hydrogen, carbon dioxide, methane or ethane, which are removed by the flasher 106. Exemplary components of liquid in line 115 are provided in Table 2. It should be understood that liquid line 115 may contain other components, not listed, such as components in the feed.

TABLE 2

FEED COMPOSITION (Liquid Stream 115)

| | Conc. (wt. %) | Conc. (wt. %) | Conc. (wt. %) |
|---|---|---|---|
| Ethanol | 5 to 70 | 10 to 60 | 15 to 50 |
| Acetic Acid | <90 | 5 to 80 | 15 to 70 |
| Water | 5 to 35 | 5 to 30 | 10 to 30 |
| Ethyl Acetate | <20 | 0.001 to 15 | 1 to 12 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout the present application are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 2 may include, but are not limited to, methanol, isopropanol, n-propanol, n-butanol or mixtures thereof. In one embodiment, the feed composition, e.g., line 115, may comprise propanol, e.g., isopropanol and/or n-propanol, in an amount from 0.001 to 0.1 wt. %, from 0.001 to 0.05 wt. % or from 0.001 to 0.03 wt. %. In should be understood that these other components may be carried through in any of the distillate or residue streams described herein and will not be further described herein, unless indicated otherwise.

When the content of acetic acid in line 115 is less than 5 wt. %, the acid separation column 107 may be skipped and line 115 may be introduced directly to second column 108, also referred to herein as a light ends column.

In the embodiment shown in FIG. 1, line 115 is introduced in the lower part of first column 107, e.g., lower half or lower third. In first column 107, unreacted acetic acid, a portion of the water, and other heavy components, if present, are removed from the composition in line 115 and are withdrawn, preferably continuously, as residue. Some or all of the residue may be returned and/or recycled back to reaction zone 101 via line 116. Recycling the acetic acid in line 116 to the vaporizer 110 may reduce the amount of heavies that need to be purged from vaporizer 110. Reducing the amount of heavies to be purged may improve efficiencies of the process while reducing byproducts.

First column 107 also forms an overhead distillate, which is withdrawn in line 117, and which may be condensed and refluxed, for example, at a ratio of from 10:1 to 1:10, e.g., from 3:1 to 1:3 or from 1:2 to 2:1.

Any of columns 107, 108, 109, or 122 may comprise any distillation column capable of separation and/or purification. The columns preferably comprise tray columns having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

Figure 2:
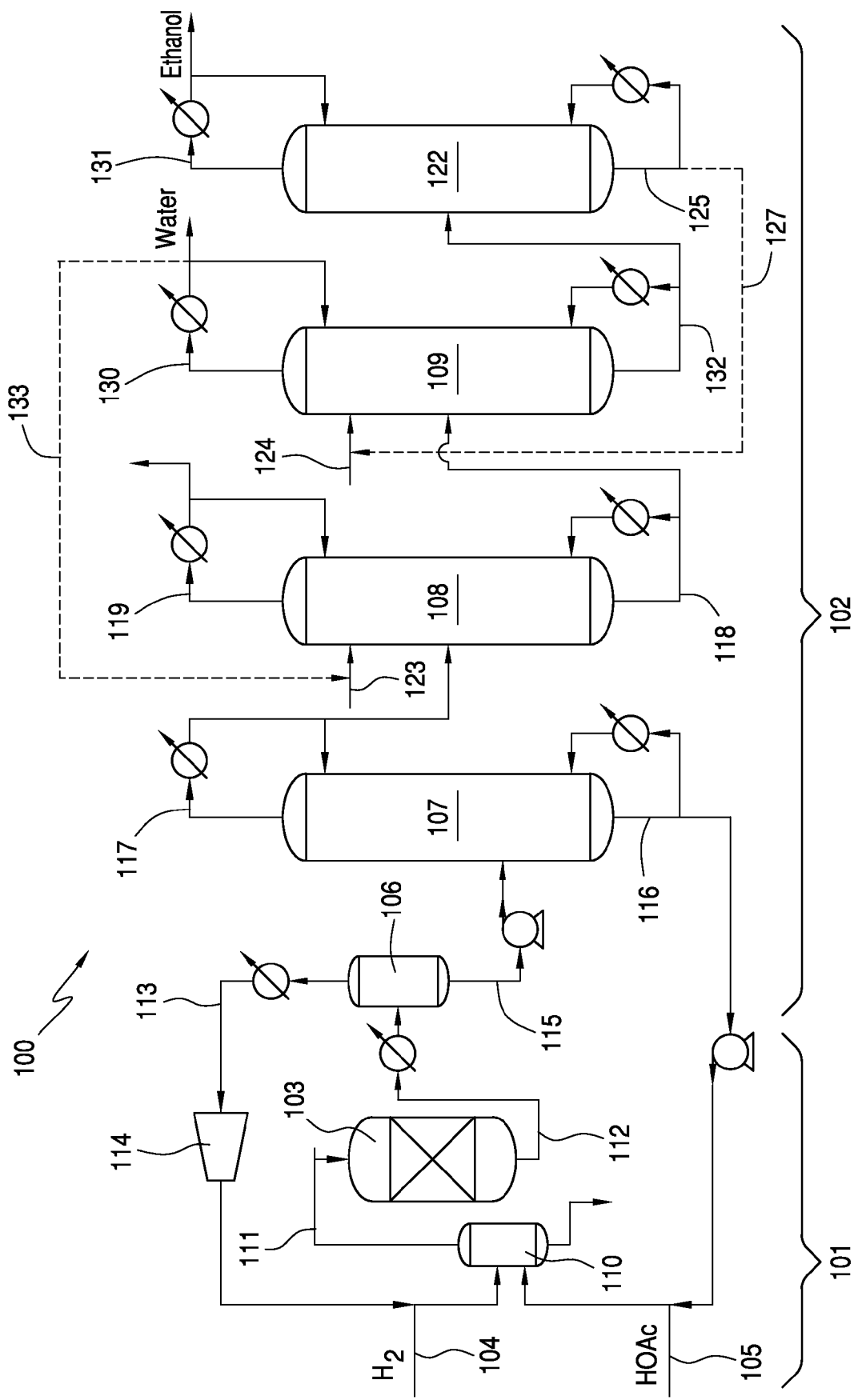
FIG. 2 is a schematic diagram of a hydrogenation system in accordance with one embodiment of the present invention.

The associated condensers and liquid separation vessels that may be employed with each of the distillation columns may be of any conventional design and are simplified in FIGS. 1-3. As shown in FIGS. 1-3, heat may be supplied to the base of each column or to a circulating bottom stream through a heat exchanger or reboiler. Other types of reboilers, such as internal reboilers, may also be used in some embodiments. The heat that is provided to reboilers may be derived from any heat generated during the process that is integrated with the reboilers or from an external source such as another heat generating chemical process or a boiler. Although one reactor and flasher are shown in FIGS. 1-3, additional reactors, flashers, condensers, heating elements, and other components may be used in embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in any of the columns may vary. As a practical matter, pressures from 10 kPa to 3000 kPa will generally be employed in these zones although in some embodiments subatmospheric pressures may be employed as well as superatmospheric pressures. Temperatures within the various zones will normally range between the boiling points of the composition removed as the distillate and the composition removed as the residue. It will be recognized by those skilled in the art that the temperature at a given location in an operating distillation column is dependent on the composition of the material at that location and the pressure of column. In addition, feed rates may vary depending on the size of the production process and, if described, may be generically referred to in terms of feed weight ratios.

When column 107 is operated under standard atmospheric pressure, the temperature of the residue exiting in line 116 from column 107 preferably is from 95° C. to 120° C., e.g., from 110° C. to 117° C. or from 111° C. to 115° C. The temperature of the distillate exiting in line 117 from column 107 preferably is from 70° C. to 110° C., e.g., from 75° C. to 95° C. or from 80° C. to 90° C. Column 107 preferably operates at ambient pressure. In other embodiments, the pressure of first column 107 may range from 0.1 kPa to 510 kPa, e.g., from 1 kPa to 475 kPa or from 1 kPa to 375 kPa. Exemplary components of the distillate and residue compositions for first column 107 are provided in Table 3 below. It should also be understood that the distillate and residue may also contain other components, not listed, such as components in the feed. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

| FIRST COLUMN | | | |
|---|---|---|---|
| | Conc. (wt. %) | Conc. (wt. %) | Conc. (wt. %) |
| Distillate | | | |
| Ethanol | 20 to 75 | 30 to 70 | 40 to 65 |
| Water | 10 to 40 | 15 to 35 | 20 to 35 |
| Acetic Acid | <2 | 0.001 to 0.5 | 0.01 to 0.2 |
| Ethyl Acetate | <60 | 5.0 to 40 | 10 to 30 |
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| Residue | | | |
| Acetic Acid | 60 to 100 | 70 to 95 | 85 to 92 |
| Water | <30 | 1 to 20 | 1 to 15 |
| Ethanol | <1 | <0.9 | <0.07 |

As shown in Table 3, without being bound by theory, it has surprisingly and unexpectedly been discovered that when any amount of acetal is detected in the feed that is introduced to the acid separation column (first column 107), the acetal appears to decompose in the column such that less or even no detectable amounts are present in the distillate and/or residue.

Depending on the reaction conditions, the crude ethanol product exiting reactor 103 in line 112 may comprise ethanol, acetic acid (unconverted), ethyl acetate, and water. After exiting reactor 103, a non-catalyzed equilibrium reaction may occur between the components contained in the crude ethanol product until it is added to flasher 106 and/or first column 107. This equilibrium reaction tends to drive the crude ethanol product to an equilibrium between ethanol/acetic acid and ethyl acetate/water, as shown below.

$$\text{EtOH} + \text{HOAc} \rightleftarrows \text{EtOAc} + \text{H}_2\text{O}$$

In the event the crude ethanol product is temporarily stored, e.g., in a holding tank, prior to being directed to distillation zone 102, extended residence times may be encountered. Generally, the longer the residence time between reaction zone 101 and distillation zone 102, the greater the formation of ethyl acetate. For example, when the residence time between reaction zone 101 and distillation zone 102 is greater than 5 days, significantly more ethyl acetate may form at the expense of ethanol. Thus, shorter residence times between reaction zone 101 and distillation zone 102 are generally preferred in order to maximize the amount of ethanol formed. In one embodiment, a holding tank (not shown), is included between the reaction zone 101 and distillation zone 102 for temporarily storing the liquid component from line 115 for up to 5 days, e.g., up to 1 day, or up to 1 hour. In a preferred embodiment no tank is included and the condensed liquids are fed directly to the first distillation column 107. In addition, the rate at which the non-catalyzed reaction occurs may increase as the temperature of the crude ethanol product, e.g., in line 115, increases. These reaction rates may be particularly problematic at temperatures exceeding 30° C., e.g., exceeding 40° C. or exceeding 50° C. Thus, in one embodiment, the temperature of liquid components in line 115 or in the optional holding tank is maintained at a temperature less than 40° C., e.g., less than 30° C. or less than 20° C. One or more cooling devices may be used to reduce the temperature of the liquid in line 115.

As discussed above, a holding tank (not shown) may be included between the reaction zone 101 and distillation zone 102 for temporarily storing the liquid component from line 115, for example from 1 to 24 hours, optionally at a temperature of about 21° C., and corresponding to an ethyl acetate formation of from 0.01 wt. % to 1.0 wt. % respectively. In addition, the rate at which the non-catalyzed reaction occurs may increase as the temperature of the crude ethanol product is increased. For example, as the temperature of the crude ethanol product in line 115 increase from 4° C. to 21° C., the rate of ethyl acetate formation may increase from about 0.01 wt. % per hour to about 0.005 wt. % per hour. Thus, in one embodiment, the temperature of liquid components in line 115 or in the optional holding tank is maintained at a temperature less than 21° C., e.g., less than 4° C. or less than −10° C.

In addition, it has now been discovered that the above-described equilibrium reaction may also favor ethanol formation in the top region of first column 107.

The distillate, e.g., overhead stream, of column 107 optionally is condensed and refluxed as shown in FIG. 1, preferably, at a reflux ratio of 1:5 to 10:1. The distillate in line 117 preferably comprises ethanol, ethyl acetate, and water, along with other impurities, which may be difficult to separate due to the formation of binary and tertiary azeotropes.

The first distillate in line 117 is introduced to the second column 108, also referred to as the "light ends column," preferably in the middle part of column 108, e.g., middle half or middle third. Preferably the second column 108 is an extractive distillation column, and an extractive agent is added thereto via lines 123 and/or 126.

Extractive distillation is a method of separating close boiling components, such as azeotropes, by distilling the feed in the presence of an extractive agent. The extractive agent preferably has a boiling point that is higher than the compounds being separated in the feed. In preferred embodiments, the extractive agent is comprised primarily of water. As indicated above, the first distillate in line 117 that is fed to the second column 108 comprises ethyl acetate, ethanol, and water. These compounds tend to form binary and ternary azeotropes, which decrease separation efficiency.

As shown, the extractive agent may be fed to second column 108 via line 123. In one embodiment, the extractive agent is provided from an external source. In other embodiments, the extractive agent may be provided via an in-process recycle stream, e.g., line 126. Of course combinations of these sources are contemplated as well. Preferably, the extractive agent is fed to second column 108 at a point higher than the first distillate in line 117. In one embodiment, the extractive agent is fed near the top of second column 108 or fed, for example, above the feed in line 117 and below the reflux line from the condensed overheads. In a tray column, the extractive agent is continuously added near the top of the second column 108 so that an appreciable amount of the extractive agent is present in the liquid phase on all of the trays below. Preferably this extractive agent comprises water. In a preferred embodiment, the extractive agent fed to second column 108 comprises at least a portion of a fourth distillate in line 126 from a fourth extractive agent recovery column 129.

The molar ratio of the water in the extractive agent to the ethanol in the feed to the second column is preferably at least 0.5:1, e.g., at least 1:1 or at least 3:1. In terms of ranges, preferred molar ratios may range from 0.5:1 to 8:1, e.g., from 1:1 to 7:1 or from 2:1 to 6.5:1.

In one embodiment, an additional extractive agent may be added to second column 108. Examples include, but are not limited to, water from an external source, dimethylsulfoxide, glycerine, diethylene glycol, 1-naphthol, hydroquinone, N,N'-dimethylformamide, 1,4-butanediol; ethylene glycol-1, 5-pentanediol; propylene glycol-tetraethylene glycol-polyethylene glycol; glycerine-propylene glycol-tetraethylene glycol-1,4-butanediol, ethyl ether, methyl formate, cyclohexane, N,N'-dimethyl-1,3-propanediamine, N,N'-dimethylethylenediamine, diethylene triamine, hexamethylene diamine and 1,3-diaminopentane, an alkylated thiopene, dodecane, tridecane, tetradecane and chlorinated paraffins. Some suitable extractive agents include those described in U.S. Pat. Nos. 4,379,028; 4,569,726; 5,993,610; and 6,375,807, the entire contents and disclosure of which are hereby incorporated by reference. The additional extractive agent may be combined with the line 123 or line 126 and co-fed to the second column 108. Additional extractive agent may also be added separately to the second column. In one aspect, the extractive agent comprises an extractive agent, e.g., water, derived from an external source via line 123 and none of the extractive agent is derived from the fourth distillate.

Although the temperature and pressure of second column 108 may vary, when at atmospheric pressure the temperature of the second residue exiting in line 118 from second column 108 preferably is from 60° C. to 90° C., e.g., from 70° C. to 90° C. or from 80° C. to 90° C. The temperature of the second distillate exiting in line 119 from second column 108 preferably is from 50° C. to 90° C., e.g., from 60° C. to 80° C. or from 60° C. to 70° C. Column 108 may operate at atmospheric pressure. In other embodiments, the pressure of second column 108 may range from 0.1 kPa to 510 kPa, e.g., from 1 kPa to 475 kPa or from 1 kPa to 375 kPa. Exemplary components for the distillate and residue compositions for second column 108 are provided in Table 4 below. It should be understood that the distillate and residue may also contain other components, not listed, such as components in the feed.

TABLE 4

| SECOND COLUMN | | | |
|---|---|---|---|
| | Conc. (wt. %) | Conc. (wt. %) | Conc. (wt. %) |
| Distillate | | | |
| Ethyl Acetate | 10 to 99 | 25 to 95 | 50 to 93 |
| Acetaldehyde | <25 | 0.5 to 15 | 1 to 8 |
| Water | <25 | 0.5 to 20 | 4 to 16 |
| Ethanol | <30 | 0.001 to 15 | 0.01 to 5 |
| Acetal | <5 | 0.001 to 2 | 0.01 to 1 |
| Residue | | | |
| Water | 30 to 90 | 40 to 85 | 50 to 85 |
| Ethanol | 10 to 75 | 15 to 60 | 20 to 50 |
| Ethyl Acetate | <3 | 0.001 to 2 | 0.001 to 0.5 |
| Acetic Acid | <0.5 | 0.001 to 0.3 | 0.001 to 0.2 |

The weight ratio of ethanol in the second residue to ethanol in the second distillate preferably is at least 3:1, e.g., at least 6:1, at least 8:1, at least 10:1 or at least 15:1. The weight ratio of ethyl acetate in the second residue to ethyl acetate in the second distillate preferably is less than 0.4:1, e.g., less than 0.2:1 or less than 0.1:1. In embodiments that use an extractive column with water as an extraction agent as the second column 108, the weight ratio of ethyl acetate in the second residue to ethyl acetate in the second distillate approaches zero.

The second distillate in line 119 preferably is refluxed as shown in FIG. 1, for example, at a reflux ratio of from 1:10 to 10:1, e.g., from 1:5 to 5:1 or from 1:3 to 3:1. The distillate from second column 108 may be purged. In one embodiment, since the second distillate contains ethyl acetate, all or a portion of the distillate from second column 108 may be recycled to reaction zone 101 in order to convert the ethyl acetate to additional ethanol (not shown). All or a portion the distillate may be recycled to reactor 103 and may be co-fed with the acetic acid feed line 105 (not shown). In another embodiment, the second distillate in line 119 may be further purified to remove impurities, such as acetaldehyde, using one or more additional columns (not shown).

As shown in FIG. 1, the second residue from the bottom of second column 108, which comprises ethanol and water, is fed via line 118 to third column 109, also referred to as the "anhydrous product column." Although FIG. 1 shows one column to represent the dehydration unit, the inventive processes may also employ separation units, e.g., dehydrators. In preferred embodiments, the dehydration unit comprises at least one extractive distillation column. Examples of suitable dehydrators include an extractive distillation column 109 (as shown in FIGS. 1 and 2); a molecular sieve unit 140 (as shown in FIG. 3); and/or a desiccant (not shown). For example, useful dehydration methods and/or units include those discussed in U.S. Pat. Nos. 4,465,875; 4,559,109; 4,654,123; and 6,375,807. The entireties of these patents are hereby incorporated by reference.

Typically, the water and the ethanol in second residue 118 form a water/ethanol azeotrope. In one embodiment, the dehydrators of the present invention remove the water from the water/ethanol azeotrope in the second residue. For example, the dehydration unit may remove at least 50 wt. % of the water from the second residue, e.g., at least 75 wt. %, at least 90 wt. %, at least 95 wt. %, or at least 99 wt. %. In terms of ranges, the dehydration removes from 50 wt. % to 100 wt. % of the water from the second residue, e.g., from 75 wt. % to 99.9999 wt. %, from 90 wt. % to 99.999 wt. %, from 90 wt. % to 99.99 wt. %, from 90 wt. % to 99.9 wt. %, or from 90 wt. % to 99.5 wt. %. The removal of this water from the second residue, in some embodiments, results in the formation of the anhydrous ethanol composition.

Stream 118 exiting second column 108 comprises primarily water, e.g., at least 50 wt. % water, e.g., at least 75 wt. %, at least 90 wt. %, at least 95 wt. %, or at least 99 wt. %, and may be removed from system 100.

In FIG. 1, the residue from second column 108, which comprises ethanol/water azeotrope, is fed, e.g., via line 118, to third column 109. Third column 109 separates, e.g., distills, water from the water/ethanol azeotrope in the second residue.

Preferably, third column 109 is an extractive distillation column that employs an extractive agent. Preferably, third column 109 operates at atmospheric pressure.

Extractive distillation is a vapor-liquid separation process, which uses an additional component to increase the relative volatility of the components to be separated. In extractive distillation, a selective high boiling solvent is utilized to alter the activity coefficients and, hence, increase the separation factor of the components. The additional component may be a liquid solvent, an ionic liquid, a dissolved salt, a mixture of volatile liquid solvent and dissolved salt, or hyperbranched polymer.

The extractive agent, e.g., the high-boiling extractive solvent, may be water selective or ethanol selective. A high-boiling water selective solvent may be employed for preferentially extracting water in column 109. The high-boiling water selective solvent preferably has a boiling point of at least 200° C. and is selected from glycerin, ethylene glycol, diethylene glycol, triethylene glycol, tetraethylene glycol, trimethylene glycol, 1,4-butanediol, and combinations thereof. When a high-boiling water selective solvent is employed, the third distillate comprises ethanol and the third residue comprises water.

A high-boiling ethanol extractive solvent may be employed for preferentially extracting ethanol in distillation column 109. The high-boiling ethanol selective solvent preferably has a boiling point of at least 200° C. and is selected from $C_{6+}$ phenols (including 2-phenyl-phenol, cumyl phenol, diisopropyl phenol and mixtures thereof), cyclic $C_7$ ketones (including cyclohexyl cyclohexanone), cyclic $C_8$ alcohols (including cyclohexyl cyclohexanol), methyl benzoate, dipropylene glycol dibenzoate, trimellitic anhydride, and mixtures thereof. Other suitable extractive agents include those described in U.S. Pat. Nos. 1,469,447; 2,591,671; 2,591,672; 2,901,404; 4,428,798; 4,455,198; 4,631,115; 4,654,123; and 6,375,807 and U.S. Pub. No. 2009/0014313, the entire contents and disclosure of which are hereby incorporated by reference. When a high-boiling ethanol selective solvent is employed, the third residue comprises ethanol and the third distillate comprises water.

Third column 109 preferably comprises from 1 to 150 trays, e.g., from 10 to 100 or from 20 to 70 trays. As indicated above, the trays may be sieve trays, fixed valve trays, movable valve trays, or any other suitable design known in the art. The extractive agent may be introduced to the third column 109 at any level. Preferably, the extractive agent is introduced into the third column 109 in the middle part of the third column 109, e.g., the middle half or middle third.

Although the temperature and pressure of third column 109 may vary, when at atmospheric pressure the temperature of the third residue exiting in line 122 from third column 109 preferably is from 60° C. to 90° C., e.g., from 70° C. to 90° C. or from 80° C. to 90° C. The temperature of the third distillate exiting in line 123 from third column 109 preferably is from 50° C. to 90° C., e.g., from 60° C. to 80° C. or from 60° C. to 70° C. Column 109 may operate at atmospheric pressure. In other embodiments, the pressure of second column 109 may range from 0.1 kPa to 510 kPa, e.g., from 1 kPa to 475 kPa or from 1 kPa to 375 kPa.

In the embodiment of FIG. 1, a high-boiling water extractive agent is employed. As a result, third column 109 recovers ethanol that has been dehydrated as the third distillate in line 121. The third residue in line 120 comprises water.

As indicated above, the second residue in line 118 that is fed to the third column 109 comprises ethanol and water. As shown in FIG. 1, in one embodiment the extractive agent comprises the fourth residue in line 127, which comprises high-boiling water extractive agent from the fourth extractive agent recovery column 122. Although, in other embodiments, an external high-boiling water extractive agent may be employed, e.g., fed via line 124. Preferably, the extractive agent, regardless of source, is fed to third column 109 at a point higher than the second residue in line 118. In one embodiment, the extractive agent is fed near the top of third column 109 or fed, for example, above the feed in line 118 and below the reflux line from the condensed overheads. In a tray column, the extractive agent is continuously added near the top of the third column 109 so that an appreciable amount of the extractive agent is present in the liquid phase on all of the trays below.

The molar ratio of the extractive agent to the ethanol in the feed to the third column is preferably at least 0.5:1, e.g., at least 1:1 or at least 3:1. In terms of ranges, preferred molar ratios may range from 0.5:1 to 8:1, e.g., from 1:1 to 7:1 or from 2:1 to 6.5:1.

In one embodiment, additional extractive agent(s) may be combined with the recycled fourth residue in line 127 and co-fed to the third column 109. The additional extractive agent may also be added separately to the third column 109. In one aspect, the extractive agent comprises an extractive agent derived from an external source via line 124 and none of the extractive agent is derived from the fourth residue.

In FIG. 1, the third residue 120 exiting the extractive distillation column comprises the third column extractive agent(s) and water, e.g., at least 50 wt. % water, e.g., at least 75 wt. %, at least 90 wt. %, at least 95 wt. %, or at least 99 wt. %, and may be removed from system 100. In one embodiment, the third residue may be fed, e.g., via line 120, to fourth column 122, also referred to as the "extractive agent recovery column," to separate water and the extractive agents.

As shown in exemplary FIG. 1, third residue may be fed via line 120 to the extractive agent recovery column 122. Fourth column 122 separates water (which can be used as a second column extractive agent) from the third column extractive agent(s). As a result, column 122 recovers water, as the distillate in line 128 and the third column extractive agent(s) as the residue in line 125. As stated above, all or part of the water-containing distillate in line 126 may be recycled to second extractive distillation column 108 and all or part of the residue in line 127, which contains third column extractive agent(s), may be recycled to third extractive distillation column 109.

As shown in FIG. 1, a portion or all of fourth distillate in line 126 from the fourth column 122 may be recycled to the second column 108. Although FIG. 1 illustrates the fourth distillate being directly recycled to the second column, in other embodiments the fourth distillate may be stored in a holding tank and indirectly recycled to the second column. In still other embodiments, only a portion, e.g., an aliquot portion, of the fourth distillate is recycled, directly or indirectly, to the second column. It is also possible to utilize water from another source via line 123 to replace a portion or all of the fourth distillate that may be fed to the second column as the extractive agent.

In preferred embodiments, the recycling of the fourth distillate promotes the separation of ethyl acetate from the residue of the second column 108. For example, the weight ratio of ethyl acetate in the second residue to second distillate preferably is less than 0.4:1, e.g., less than 0.2:1 or less than 0.1:1. In embodiments that use an extractive distillation column with water as an extractive agent as the second column 108, the weight ratio of ethyl acetate in the second residue to ethyl acetate in the second distillate approaches zero.

All or a portion of the fourth distillate is recycled to the second column. In one embodiment, all of the fourth distillate may be recycled until process 100 reaches a steady state and then a portion of the fourth distillate is recycled with the remaining being purged from the system 100 in line 128. The composition of the second residue will tend to have lower amounts of ethanol than when the fourth distillate is not recycled. As the fourth distillate is recycled, the composition of the second residue, as provided in Table 2, comprises less than 30 wt. % of ethanol, e.g., less than 20 wt. % or less than 15 wt. %. The majority of the second residue preferably comprises water. Notwithstanding this effect, the extractive distillation step advantageously also reduces the amount of ethyl acetate that is sent to the third column, which is highly beneficial in ultimately forming a highly pure ethanol product.

In FIG. 2, another exemplary embodiment, where a high-boiling ethanol selective agent is employed, the third residue 132 comprises anhydrous ethanol and the extractive agent. As shown in FIG. 2, water is removed as the third distillate 130. Thus, when an ethanol selective extractive agent is employed, as opposed to a water selective extractive agent as in FIG. 1, the components of the third column distillate and residue are essentially reversed.

All or a portion of the third distillate may be returned, e.g., via optional line 133, to second column 108 for use as the extractive agent.

The third residue 132 may be fed to fourth distillation column 122 to separate anhydrous ethanol, which exits via line 131, from the third column extractive agent, which exits in line 125. All or a portion of the third column extractive agent in line 125 may be recycled to third column 109. Optionally, the extractive agent in line 125 may be combined with additional extractive agent from external source 124.

In another embodiment the ethanol-containing stream exiting the third column extractive agent may be fed to a molecular sieve unit comprising molecular sieves. In these embodiments, the molecular sieves further separate water from the ethanol-containing stream. In some embodiments, a molecular sieve unit may be used in conjunction with the anhydrous ethanol column. Generally speaking, the molecular sieves may be configured in a molecular sieve bed (not shown). In one embodiment, the molecular sieves are selected to remove one or more impurities that may exist in the second residue. The selection criteria may include, for example, pore size and volume characteristics. In one embodiment, the molecular sieve material is selected to remove water, acetic acid, and/or ethyl acetate from the second residue to form the anhydrous ethanol composition. Suitable molecular sieves include, for example, zeolites and molecular sieves 3A, 4A and 5A (commercially available from Aldrich). In another embodiment, an inorganic adsorbent such as lithium chloride, silica gel, activated alumina, and/or bio-based adsorbents such as corn grits, may be utilized. In a preferred embodiment, molecular sieve unit 140 removes water from the second residue in the amounts discussed above.

In addition, other separation units, e.g., dehydrating units, such as desiccant systems and/or membrane systems, may be used, either in place of or in conjunction with the finishing column and/or the molecular sieve unit discussed above. If multiple dehydrating units are utilized, the dehydrating units, being of the same or of different type, may be utilized in any configuration. Preferably, an extractive distillation column and a membrane system are utilized with one another. Optionally, the molecular sieves are employed in a bed within the finishing column, e.g., at the upper portion thereof.

Other exemplary dehydration processes include azeotropic distillation and membrane separation. In azeotropic distillation, a volatile component, often referred to as an entrainer, is added to the components to be separated. The addition of the entrainer forms an azeotrope with the components, thus changing the relative volatilities thereof. As a result, the separation factors (activity coefficients) of the components are improved. The azeotropic distillation system, in one embodiment, comprises one or more distillation columns, e.g., two or more or three or more.

Membrane separation, e.g., membrane pervaporation, may also be an effective and energy-saving process for separating azeotropic mixtures. Generally speaking, pervaporation is based on the solution-diffusion mechanism, which relies on the gradient of the chemical potential between the feed and the permeate sides of the membrane. The membranes, in one embodiment, may be hydrophilic or hydrophobic. Preferably, the membranes are hydrophilic or water permselective due to the smaller molecular size of water. In other embodiments, the membranes are hydrophobic or ethanol permselective. Typically, there are three categories of membranes that may be used—inorganic, polymeric, and composite membrane.

Anhydrous Ethanol Composition

The anhydrous ethanol compositions in line 121 (FIG. 1) or line 131 (FIG. 2) beneficially comprise ethanol and, if any, a small amount of water preferably formed via the inventive acetic acid hydrogenation and separation steps. In one embodiment, the term "anhydrous ethanol composition," as used herein, means a substantially anhydrous ethanol composition. Table 5 provides exemplary ranges for the water concentration in the anhydrous ethanol compositions. Although Table 5 indicated that water is preferably present in a small amount, in other embodiments, the anhydrous ethanol composition may be completely anhydrous, e.g., containing no detectable water. In these cases conventional water detection methods employed in the industry may be utilized to measure water content or lack thereof. Preferably, the anhydrous ethanol composition comprises at least 95 wt. % ethanol, e.g., at least 95 wt. %, at least 99 wt. %, at least 99.9 wt. %, or at least 99.99 wt. %. Table 6 provides exemplary ranges for the ethanol concentration in the anhydrous ethanol compositions.

In addition to the ethanol and, if any, a small amount of water, the anhydrous ethanol composition may also comprise only trace amounts of other impurities such as acetic acid; $C_3$ alcohols, e.g., n-propanol; and/or $C_4$-$C_5$ alcohols. Exemplary compositional ranges for the ethanol, the water, and various impurities that may be present in small amounts, if at all, are provided below in Table 5.

TABLE 5

ANHYDROUS ETHANOL COMPOSITIONS

| Component | Conc. (wt. %) | Conc. (wt. %) | Conc. (wt. %) |
|---|---|---|---|
| Ethanol | 95 to 100 | 95 to 99.99 | 99 to 99.90 |
| Water | 0.0001 to 1 | 0.001 to 0.5 | 0.001 to 0.05 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The anhydrous ethanol compositions of the present invention preferably contain very low amounts, e.g., less than 0.5 wt. %, of other alcohols, such as methanol, butanol, isobutanol, isoamyl alcohol and other $C_4$-$C_{20}$ alcohols.

The anhydrous ethanol compositions of the embodiments of the present invention may be suitable for use in a variety of applications including fuels, solvents, chemical feedstocks, pharmaceutical products, cleansers, sanitizers, or hydrogenation transport. In fuel applications, the anhydrous ethanol composition may be blended with gasoline for motor vehicles such as automobiles, boats and small piston engine aircraft. In non-fuel applications, the anhydrous ethanol composition may be used as a solvent for toiletry and cosmetic preparations, detergents, disinfectants, coatings, inks, and pharmaceuticals. The anhydrous ethanol composition may also be used as a processing solvent, e.g., in manufacturing processes for medicinal products, food preparations, dyes, photochemicals and latex processing.

The anhydrous ethanol composition may also be used as a chemical feedstock to make other chemicals such as vinegar, ethyl acrylate, ethyl acetate, ethylene, glycol ethers, ethylamines, aldehydes, and higher alcohols, especially butanol. The anhydrous ethanol composition may be suitable for use as a feed stock in esters production. Preferably, in the production of ethyl acetate, the anhydrous ethanol composition may be esterified with acetic acid or reacted with polyvinyl acetate. The anhydrous ethanol composition may be dehydrated to produce ethylene. Any of known dehydration catalysts can be employed to dehydrate ethanol, such as those described in copending U.S. Pub. No. 20100030001 and 20100030002, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated by reference.

While the invention has been described in detail, modifications within the spirit and scope of the invention will be readily apparent to those of skill in the art. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with one or more other embodiments, as will be appreciated by one of skill in the art. Furthermore, those of ordinary skill in the art will appreciate that the foregoing description is by way of example only, and is not intended to limit the invention.

We claim:

1. A process for producing ethanol, the process comprising the steps of:
   hydrogenating acetic acid in the reactor in the presence of a catalyst to form a crude ethanol product;
   separating at least a portion of the crude ethanol product in a first distillation column to yield a first distillate comprising ethanol, ethyl acetate, and water, and a first residue comprising acetic acid;
   separating at least a portion of the first distillate in a second distillation column to yield a second distillate comprising ethyl acetate and a second residue comprising ethanol and water, wherein the second distillation column is an extractive distillation; and
   dehydrating at least a portion of the second residue via extractive distillation to yield an anhydrous ethanol composition comprising less than 1 wt. % water;
   wherein a first extractive agent is used to extract ethanol or water from the second residue; a second extractive agent comprising water is fed to the second distillation column; and wherein the first extractive agent is different than the second extractive agent.

2. The process of claim 1, wherein the anhydrous ethanol composition comprises less than 0.1 wt. % water.

3. The process of claim 1, wherein the anhydrous ethanol composition comprises:
   from 95 wt. % to 99.9999 wt. % ethanol; and
   from 0.0001 wt. % to 1 wt. % water.

4. The process of claim 1, wherein the dehydrating removes at least 50 wt. % of the water from the second residue.

5. The process of claim 1, wherein the dehydrating comprises separating, in a third column, at least a portion of the second residue into a third distillate and a third residue, wherein the third column comprises an extractive distillation column that employs the first extractive agent.

6. The process of claim 5, wherein the first extractive agent is high boiling water selective agent.

7. The process of claim 6, wherein the first extractive agent is selected from the group consisting of glycols, glycerol, gasoline, hexane, and combinations thereof.

8. The process of claim 7, wherein the third distillate comprises the anhydrous ethanol composition comprising from 0.001 wt. % to 0.5 wt. % water.

9. The process of claim 5, wherein the first extractive agent is high boiling ethanol selective agent.

10. The process of claim 9, wherein and the third residue comprises the anhydrous ethanol composition comprising from 0.001 wt. % to 0.5 wt. % water.

11. The process of claim 5, wherein the dehydrating yields an extractive agent stream comprising the first extractive agent.

12. The process of claim 11, further comprising recovering the first extractive agent from the extractive agent stream.

13. The process of claim 1, wherein the dehydrating comprises separating, in a third distillation column, at least a portion of the second residue into a third distillate and a third residue.

14. The process of claim 13, wherein the second extractive agent comprises at least a portion of the third residue.

15. A process for producing ethanol, the process comprising the steps of:
    hydrogenating acetic acid in the reactor in the presence of a catalyst to form a crude ethanol product;
    separating at least a portion of the crude ethanol product to yield a first distillate comprising ethanol, ethyl acetate and water;
    separating at least a portion of the first distillate in a second distillation column to yield a second distillate comprising ethyl acetate and a second residue comprising ethanol and water, wherein the second distillation column is an extractive distillation;
    separating at least a portion of the second residue in a third distillation column a third distillate comprising ethanol and a third residue comprising water; and
    dehydrating at least a portion of the third distillate via extractive distillation to yield an anhydrous ethanol composition comprising less that 1 wt. % water and an extractive agent stream comprising a first extractive agent;
    wherein the first extractive agent is used to extract water from the second residue;
    wherein a second extractive agent comprising water is fed to the second distillation column; and
    wherein the first extractive agent is different than the second extractive agent.

16. The process of claim 15, wherein the second extractive agent comprises at least a portion of the third residue.

17. The process of claim 15, wherein the first extractive agent is high boiling water selective agent.

18. The process of claim 15, wherein the first extractive agent is selected from the group consisting of glycols, glycerol, gasoline, hexane, and combinations thereof.

\* \* \* \* \*